United States Patent
Ito et al.

(10) Patent No.: US 7,517,990 B2
(45) Date of Patent: Apr. 14, 2009

(54) METHOD FOR DEUTERATION OF A HETEROCYCLIC RING

(75) Inventors: Nobuhiro Ito, Kawagoe (JP); Tsuneaki Maesawa, Kawagoe (JP); Kazushige Muto, Kawagoe (JP); Kosaku Hirota, Gifu (JP); Hironao Sajiki, Gifu (JP)

(73) Assignee: Wako Pure Chemical Industries, Ltd., Osaka-shi, Osaka (JP)

( * ) Notice: Subject to any disclaimer, the term of this patent is extended or adjusted under 35 U.S.C. 154(b) by 586 days.

(21) Appl. No.: 10/534,344

(22) PCT Filed: Nov. 7, 2003

(86) PCT No.: PCT/JP03/14181

§ 371 (c)(1),
(2), (4) Date: May 9, 2005

(87) PCT Pub. No.: WO2004/046066

PCT Pub. Date: Jun. 3, 2004

(65) Prior Publication Data

US 2006/0025596 A1 Feb. 2, 2006

(30) Foreign Application Priority Data

Nov. 15, 2002 (JP) .............................. 2002-331594

(51) Int. Cl.
*C07D 295/03* (2006.01)
*C07D 207/06* (2006.01)
(52) U.S. Cl. ...................................... 546/184; 548/400
(58) Field of Classification Search ................. 546/184; 548/400
See application file for complete search history.

(56) References Cited

U.S. PATENT DOCUMENTS

| 3,849,458 A | 11/1974 | Dinh-Nguyen et al. |
| 4,874,890 A | 10/1989 | Kato et al. |
| 4,880,941 A | 11/1989 | Shroot et al. |

FOREIGN PATENT DOCUMENTS

| GB | 1 103 607 | * 2/1968 |
| JP | 45-17402 | 6/1976 |
| JP | 60-248666 | 12/1985 |
| JP | 61-275241 | 5/1986 |
| JP | 61-277648 | 12/1986 |
| JP | 63-198638 | 8/1988 |
| JP | 5-19536 | 3/1993 |

OTHER PUBLICATIONS

Kiuru et al. "Deuteration of Estrogens using Pd/C as a Catalyst" Synthesis and Applications of Isotopically Labelled Compounds 1997: Proceedings of the Sixth International Symposium, Philadelphia, USA, Sep. 14-18, 1997, (1998) p. 475-477.
"Biosynthesis of luciferin in the sea firefly, *Cypridina hilgendorfii*: L-tryptophan is a component in *Cypridina luciferin*", Oba et al., Tetrahedron Letters 43 (2002) 2389-2392.
"Hydrogen isotope exchange reactions involving C-H (D,T) bonds", Junk et al., Chemical Society Reviews, 1997, vol. 26, 401-406.
"A highly efficient synthetic procedure for deuteriating imidazoles and imidazolium salts", Hardacre et al., Chem. Commun., 2001, 367-368.
Garnett, Henderson, Sollich, Van Dyke Tiers: "An NMR study of orientation effects in the catalytic deuteration and tritiation of aromatic compounds. Simplification of spin-coupled NMR spectra by the method of massive deuteration" Tetrahedron Letters, vol. 2, 1961, pp. 516-522, XP002388045 p. 517, last paragraph; tables 2, last, entry.
Elvidge, Jones, Mane, Al Rawi: "Tritiun nuclear magnetic resonance spectroscopy. Par 10. Distribution of Tritium in some labelled nitrogen heterocyclic compounds" J. Chem. Soc. Perkin Transactions 2, 1979, pp. 386-388, XP009068654 Experimental table.
Sajiki, Hattori, Aoki, Yasunaga, Hirota: "Pd/C-H2-Catalysed Deuterium exchange reaction of the benzylic site in D20" Synlett, Jul. 1, 2002, pp. 1149-1151, XP002388047 table 1.
"Iridium-Catalyzed H/D Exchange into Organic Compounds in Water", Klei et al., J. Am. Chem. Soc. vol. 24, No. 10, 2002, pp. 2092-2093.
"Preparation of Fully Deuterated Fatty Acids by Simple Method". Hsiao et al., Lipids, vol. 9, No. 11, p. 913, 1974.
Hardacre, Holbrey, McMath: "A highly efficient synthetic procedure for deuteriating imidazoles and imidazolium salts" Chem. Commun., 2001, pp. 367-368, XP002388046 the whole document.

* cited by examiner

*Primary Examiner*—James O Wilson
*Assistant Examiner*—Ebenezer Sackey
(74) *Attorney, Agent, or Firm*—Hamre, Schumann, Mueller & Larson, P.C.

(57) ABSTRACT

The present invention relates to a method for deuteration of a heterocyclic ring, which comprises subjecting a compound having a heterocyclic ring to sealed refluxing state in a deuterated solvent in the presence of an activated catalyst selected form a palladium catalyst, a platinum catalyst, a rhodium catalyst, a ruthenium catalyst, a nickel catalyst and a cobalt catalyst. In accordance with a method of the present invention, a hydrogen atom belonging to a heterocyclic ring of a compound having a heterocyclic ring can be very efficiently deuterated because temperature of deuteration reaction can be maintained at higher than boiling point of the solvent.

Further, a method for deuteration of the present invention can be applied widely to deuteration of various compounds having a heterocyclic ring which are liable to decomposition under supercritical conditions or acidic conditions, leading to industrial and efficient deuteration of a compound having a heterocyclic ring.

5 Claims, No Drawings

METHOD FOR DEUTERATION OF A HETEROCYCLIC RING

TECHNICAL FIELD

The present invention relates to a method for deuteration of a heterocyclic ring, using an activated catalyst.

BACKGROUND OF THE INVENTION

A compound having a heavy hydrogen (deuterium and tritium) is said to be useful in various purposes. For example, a deuterated compound is very useful in elucidation of reaction mechanism and substance metabolism and used widely as a labeled compound. Said compound is also known to be useful as drugs, pesticides, organic EL materials, and the like due to change in stability and property itself by isotope effect thereof. A compound having tritium also is said to be useful as a labeled compound in animal tests and the like to survey absorption, distribution, concentration in blood, excretion, metabolism and the like of drugs, etc. Therefore, research on a compound having a heavy hydrogen (deuterium and tritium) has been increasing also in these fields.

Various methods for obtaining these compounds having a heavy hydrogen have conventionally been used, however, among others, there are many problems to be solved in deuteration technology of a heterocyclic ring, and it was difficult to efficiently and industrially obtain a compound having a deuterated heterocyclic ring.

Conventional technology includes, for example, a method for deuteration of a compound having a heterocyclic ring using heavy water, deuterated hydrochloric acid and mercaptoacetic acid [Tetrahedron Letters, 43 (2002), 2389-2392], a method for deuteration of a compound having a heterocyclic ring under a supercritical condition using supercritical heavy water and deuterated anion (Chemical Society Reviews, 1997, Volume 26, 401-406), and a method for deuteration of a compound having a heterocyclic ring at 100° C. using a palladium catalyst reduced with hydrogen gas in advance (Chem. Commun., 2001, 367-368).

However, a method containing the addition process of an acid to a reaction system is not only impossible to deuterate a compound having a heterocyclic ring labile to decomposition under acidic condition but also has a problem that a complicated purifying procedure is required to isolate a deuterated compound by said method because the reaction liquid is not neutral, even if a compound which does not decompose in acidic condition is used as a substrate.

Further, a method using supercritical heavy water has problems that a compound to be a reaction substrate tends to be easily decomposed due to very high reactivity of the supercritical water, as well as that the reaction itself must be conducted under a severe condition such as supercritical condition.

Furthermore, a method wherein the deuteration reaction is conducted at 100° C. using a palladium catalyst reduced with hydrogen gas in advance and heavy water requires a complicated procedure that the palladium catalyst reduced with hydrogen gas has to be freeze-pumped repeatedly before use for the deuteration reaction.

In view of the above situation, development of a method is needed for deuteration of a compound having a heterocyclic ring efficiently and industrially irrespective of presence and non-presence of a substituent or types thereof.

SUMMARY OF THE INVENTION

The present invention relates to a method for deuteration of a heterocyclic ring, characterized by subjecting a compound having a heterocyclic ring to sealed refluxing state in a deuterated solvent in the presence of an activated catalyst selected from a palladium catalyst, a platinum catalyst, a rhodium catalyst, a ruthenium catalyst, a nickel catalyst and a cobalt catalyst.

BEST MODE FOR CARRYING OUT OF THE INVENTION

In the present invention, heavy hydrogen means deuterium (D) and tritium (T) and deuteration means substitution with deuterium and tritium. Further, in the present specification, deuteration ratio means ratio of amount of hydrogen atom substituted by a deuterium or a tritium atom to amount of hydrogen atom in a compound having a heterocyclic ring.

In a method for deuteration of the present invention, a compound having a heterocyclic ring includes a compound having a heterocyclic ring containing not less than 1 hetero atom, preferably 1 to 3 hetero atoms and not less than 1 hydrogen atom present on said heterocyclic ring.

The hetero atom contained in a heterocyclic ring includes generally a nitrogen atom, an oxygen atom, a sulfur atom and the like, and among others, a nitrogen atom is preferable.

The heterocyclic ring as described above includes generally 3- to 20-membered, preferably 3- to 14-membered, more preferably 5- to 10-membered monocyclic heterocyclic ring or polycyclic heterocyclic ring, which may have aromatic properties. Further, the heterocyclic ring is, in the case of a monocyclic heterocyclic ring, still more preferably 5- to 6-membered, and in the case of a polycyclic heterocyclic ring, still more preferably 9- to 10-membered and particularly preferably 9-membered. These heterocyclic rings may be condensed in straight chained state, branched state or cyclic state and may take plane structure or stereo structure.

Further, said heterocyclic ring may have generally 1 to 5, preferably 1 to 2, more preferably 1 substituent.

Specific examples of the monocyclic heterocyclic ring include, for example, 3-membered heterocyclic rings having one hetero atom such as oxirane ring and aziridine ring; 5-membered heterocyclic rings having one hetero atom such as furan ring, thiophene ring, pyrrole ring, 2H-pyrrole ring, pyrroline ring, 2-pyrroline ring and pyrrolidine ring; 5-membered heterocyclic rings having two hetero atoms such as 1,3-dioxolan ring, oxazole ring, isooxazole ring, 1,3-oxazole ring, thiazole ring, isothiazole ring, 1,3-thiazole ring, imidazole ring, imidazoline ring, 2-imidazoline ring, imidazolidine ring, pyrazole ring, pyrazoline ring, 3-pyrazoline ring and pyrazolidine ring; 5-membered heterocyclic rings having three hetero atoms such as furazan ring, triazole ring, thiadiazole ring and oxadiazole ring; 6-membered heterocyclic rings having one hetero atom such as pyran ring, 2H-pyran ring, pyridine ring and piperidine ring; 6-membered heterocyclic rings having two hetero atoms such as thiopyrane ring, pyridazine ring, pyrimidine ring, pyrazine ring, piperazine ring and morpholine ring; 6-membered heterocyclic rings having three hetero atoms such as 1,2,4-triazine ring.

The polycyclic heterocyclic ring includes one wherein 2 to 3 monocyclic heterocyclic rings are condensed each other, or a bicyclic heterocyclic ring or a tricyclic heterocyclic ring, wherein a monocyclic heterocyclic ring is condensed with 1 to 2 aromatic rings such as a benzene ring and a naphthalene ring.

Specific examples of the bicyclic heterocyclic ring include, for example, heterocyclic rings having one hetero atom such as benzofuran ring, isobenzofuran ring, 1-benzothiophene ring, 2-benzothiophene ring, indole ring, 3-indole ring, isoindole ring, indolizine ring, indoline ring, isoindoline ring, 2H-chromene ring, chroman ring, isochroman ring, 1H-2-benzopyran ring, quinoline ring, isoquinoline ring and 4H-quinolizine ring; heterocyclic rings having two hetero atoms such as benzoimidazole ring, benzothiazole ring, 1H-indazole ring, 1,8-naphthyridine ring, quinoxaline ring, quinazoline ring, quinazolidine ring, cinnoline ring and phthalazine ring; heterocyclic rings having four hetero atoms such as purine ring and pteridine ring.

Specific examples of the tricyclic heterocyclic ring include, for example, heterocyclic rings having one hetero atom such as carbazole ring, 4aH-carbazole ring, xanthene ring, phenanthridine ring and acridine ring; heterocyclic rings having two hetero atoms such as β-carboline ring, perimidine ring, 1,7-phenanthroline ring, 1,10-phenanthroline ring, thianthrene ring, phenoxathiin ring, phenoxazine ring, phenothiazine ring and phenazine ring.

Specific examples of the substituent of the above heterocyclic ring which may have a substituent include, for example, a halogen atom, a hydroxyl group, a mercapto group, an oxo group, a thioxo group, a carboxyl group, a sulfo group, a sulfino group, a sulfeno group, a phosphino group, a phosphinoyl group, a formyl group, an amino group, a cyano group and a nitro group, and moreover an alkyl group, an alkenyl group, an aryl group, an aralkyl group, an alkoxy group, an aryloxy group, an alkylthio group, an arylthio group, an alkylsulfonyl group, an arylsulfonyl group, an alkylsulfinyl group, an arylsulfinyl group, an alkylphosphino group, an arylphosphino group, an alkylphosphinoyl group, an arylphosphinoyl group, an alkylamino group, an arylamino group, an alkoxycarbonyl group, an aryloxycarbonyl group, an alkoxysulfonyl group, an aryloxysulfonyl group, an acyl group and an acyloxy group, which may further have a substituent.

The above alkyl group may be straight chained, branched or cyclic, and includes one generally having 1 to 20, preferably 1 to 15, more preferably 1 to 10 and further preferably 1 to 6 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a 3-methylpentyl group, a 2-methylpentyl group, a 1,2-dimethylbutyl group, a n-heptyl group, an isoheptyl group, a sec-heptyl group, an n-octyl group, an isooctyl group, a sec-octyl group, a n-nonyl group, a n-decyl group, an n-undecyl group, a n-dodecyl group, a n-tridecyl group, a n-tetradecyl group, a n-pentadecyl group, a n-hexadecyl group, a n-heptadecyl group, an n-octadecyl group, a n-nonadecyl group, an n-icosyl group, a cyclopropyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group, a cyclooctadecyl group, a cyclononadecyl group and a cycloicosyl group.

The alkenyl group may be straight chained, branched or cyclic, and includes one generally having 2 to 20, preferably 2 to 10 and more preferably 2 to 6 carbon atoms, and having not less than 1 carbon-carbon double bond in the chain of the above alkyl group having not less than 2 carbon atoms, among the above alkyl groups, which is specifically exemplified by a vinyl group, an allyl group, a 1-propenyl group, an isopropenyl group, a 3-butenyl group, a 2-butenyl group, a 1-butenyl group, a 1,3-butadienyl group, a 4-pentenyl group, a 3-pentenyl group, a 2-pentenyl group, a 1-pentenyl group, a 1,3-pentadienyl group, a 2,4-pentadienyl group, a 1,1-dimethyl-2-propenyl group, an 1-ethyl-2-propenyl group, a 1,2-dimethyl-1-propenyl group, a 1-methyl-1-butenyl group, a 5-hexenyl group, a 4-hexenyl group, a 2-hexenyl group, a 1-hexenyl group, a 1-methyl-1-hexenyl group, a 2-methyl-2-hexenyl group, a 3-methyl-1,3-hexadienyl group, a 1-heptenyl group, an 2-octenyl group, a 3-nonenyl group, a 4-decenyl group, a 1-dodecenyl group, a 1-tetradecenyl group, a 1-hexadecenyl group, an 1-octadecenyl group, a 1-icosenyl group, a 1-cyclopropenyl group, a 2-cyclopentenyl group, a 2,4-cyclopentadienyl group, a 1-cyclohexenyl group, a 2-cyclohexenyl group, a 3-cyclohexenyl group, a 2-cycloheptenyl group, a 2-cyclononenyl group, a 3-cyclodecenyl group, a 2-cyclotridecenyl group, a 1-cyclohexadecenyl group, a 1-cyclooctadecenyl group and a 1-cycloicosenyl group.

The aryl group includes one generally having 6 to 14, preferably 6 to 10 carbon atoms, which is specifically exemplified by a phenyl group, a naphthyl group and an anthryl group.

The aralkyl group may be straight chained, branched or cyclic, and includes one generally having 7 to 34, preferably 7 to 20 and more preferably 7 to 15 carbon atoms, which is the above alkyl group substituted with the above aryl group, which is specifically exemplified by a benzyl group, a phenylethyl group, a phenylpropyl group, a phenylbutyl group, a phenylpentyl group, a phenylhexyl group, a phenylheptyl group, a phenyloctyl group, a phenylnonyl group, a phenyldecyl group, a phenylundecyl group, a phenyldodecyl group, a phenyltridecyl group, a phenyltetradecyl group, a phenylpentadecyl group, a phenylhexadecyl group, a phenylheptadecyl group, a phenyloctadecyl group, a phenylnonadecyl group, a phenylicosyl group, a naphthylethyl group, a naphthylpropyl group, a naphthylbutyl group, a naphthylpentyl group, a naphthylhexyl group, a naphthylheptyl group, a naphthyloctyl group, a naphthylnonyl group, a naphthyldecyl group, a naphthylundecyl group, a naphthyldodecyl group, a naphthyltridecyl group, a naphthyltetradecyl group, a naphthylpentadecyl group, a naphthylhexadecyl group, a naphthylheptadecyl group, a naphthyloctadecyl group, a naphthylnonadecyl group, a naphthylicosyl group, an anthrylethyl group, an anthrylpropyl group, an anthrylbutyl group, an anthrylpentyl group, an anthrylhexyl group, an anthrylheptyl group, an anthryloctyl group, an anthrylnonyl group, an anthryldecyl group, an anthrylundecyl group, an anthryldodecyl group, an anthryltridecyl group, an anthryltetradecyl group, an anthrylpentadecyl group, an anthrylhexadecyl group, an anthrylheptadecyl group, an anthryloctadecyl group, an anthrylnonadecyl group, an anthrylicosyl group, a phenanthrylethyl group, a phenanthrylpropyl group, a phenanthrylbutyl group, a phenanthrylpentyl group, a phenanthrylhexyl group, a phenanthrylheptyl group, a phenanthryloctyl group, a phenanthrylnonyl group, a phenanthryldecyl group, a phenanthrylundecyl group, a phenanthryldodecyl group, a phenanthryltridecyl group, a phenanthryltetradecyl group, a phenanthrylpentadecyl group, a phenanthrylhexadecyl group, a phenanthrylheptadecyl group, a phenanthryloctadecyl group, a phenanthrylnonadecyl group and a phenanthrylicosyl group.

The alkoxy group may be straight chained, branched or cyclic, and includes one generally having 1 to 20, preferably 1 to 15, more preferably 1 to 10 and further preferably 1 to 6 carbon atoms, which is specifically exemplified by a methoxy group, an ethoxy group, a propoxy group, an isopropoxy group, a butoxy group, an isobutoxy group, a sec-butoxy group, a tert-butoxy group, a pentyloxy group, a neopentyloxy group, a hexyloxy group, an isohexyloxy group, a tert-hexyloxy group, a heptyloxy group, an octyloxy group, a nonyloxy group, a decyloxy group, an undecyloxy group, a tetradecyloxy group, a hexadecyloxy group, a heptadecyloxy group, a nonadecyloxy group, an icosyloxy group, a cyclohexyloxy group, a cyclooctyloxy group, a cyclodecyloxy group and a cyclononadecyloxy group.

The aryloxy group includes one generally having 6 to 14, preferably 6 to 10 carbon atoms, which is specifically exemplified by a phenoxy group, a naphthyloxy group and an anthryloxy group.

The alkylthio group may be straight chained, branched or cyclic, and includes one generally having 1 to 20, preferably 1 to 15, more preferably 1 to 10 and further preferably 1 to 6 carbon atoms, wherein an oxygen atom in the above alkoxy group is replaced by a sulfur atom, which is specifically exemplified by a methylthio group, an ethylthio group, a propylthio group, an isopropylthio group, a butylthio group, an isobutylthio group, a tert-butylthio group, a pentylthio group, a hexylthio group, an octylthio group, a nonylthio group, a decylthio group, a tridecylthio group, a tetradecylthio group, a hexadecylthio group, an octadecylthio group, an icosylthio group, a cyclohexylthio group, a cyclodecylthio group and a cycloheptadecylthio group.

The arylthio group includes one wherein an alkyl group in the above alkylthio group is replaced by the above aryl group, which is specifically exemplified by a phenylthio group, a naphthylthio group and an anthrylthio group.

The alkylsulfonyl group may be straight chained, branched or cyclic, and includes one generally having 1 to 20, preferably 1 to 15, more preferably 1 to 10 and further preferably 1 to 6 carbon atoms, which is specifically exemplified by a methylsulfonyl group, an ethylsulfonyl group, a n-propylsulfonyl group, an isopropylsulfonyl group, a n-butylsulfonyl group, an isobutylsulfonyl group, a tert-butylsulfonyl group, a pentylsulfonyl group, a neopentylsulfonyl group, a hexylsulfonyl group, an isohexylsulfonyl group, a tert-hexylsulfonyl group, a heptylsulfonyl group, an octylsulfonyl group, a nonylsulfonyl group, a decylsulfonyl group, an undecylsulfonyl group, a tetradecylsulfonyl group, a hexadecylsulfonyl group, a heptadecylsulfonyl group, a nonadecylsulfonyl group, an icosylsulfonyl group, a cyclohexylsulfonyl group, a cyclooctylsulfonyl group, a cyclodecylsulfonyl group and a cyclononadecylsulfonyl group.

The arylsulfonyl group includes one generally having 6 to 14, preferably 6 to 10 carbon atoms, which is specifically exemplified by a phenylsulfonyl group, a naphthylsulfonyl group and an anthrylsulfonyl group.

The alkylsulfinyl group may be straight chained, branched or cyclic, and includes one generally having 1 to 20, preferably 1 to 15, more preferably 1 to 10 and further preferably 1 to 6 carbon atoms, which is specifically exemplified by a methylsulfinyl group, an ethylsulfinyl group, a n-propylsulfinyl group, an isopropylsulfinyl group, a n-butylsulfinyl group, an isobutylsulfinyl group, a tert-butylsulfinyl group, a pentylsulfinyl group, a neopentylsulfinyl group, a hexylsulfinyl group, an isohexylsulfinyl group, a tert-hexylsulfinyl group, a heptylsulfinyl group, an octylsulfinyl group, a nonylsulfinyl group, a decylsulfinyl group, an undecylsulfinyl group, a tetradecylsulfinyl group, a hexadecylsulfinyl group, a heptadecylsulfinyl group, a nonadecylsulfinyl group, an icosylsulfinyl group, a cyclohexylsulfinyl group, a cyclooctylsulfinyl group, a cyclodecylsulfinyl group and a cyclononadecylsulfinyl group.

The arylsulfinyl group includes one, wherein the alkyl group in the above alkylsulfinyl group is replaced by the above aryl group, which is specifically exemplified by a phenylsulfinyl group, a naphthylsulfinyl group and an anthrylsulfinyl group.

The alkylphosphino group includes one, wherein one or two of hydrogen atoms of a phosphino group is each independently replaced by the above alkyl group, which is specifically exemplified by a methylphosphino group, an ethylphosphino group, a n-propylphosphino group, an isopropylphosphino group, a n-butylphosphino group, an isobutylphosphino group, a tert-butylphosphino group, a pentylphosphino group, a hexylphosphino group, a heptylphosphino group, an octylphosphino group, a nonylphosphino group, a decylphosphino group, a dodecylphosphino group, a tetradecylphosphino group, a pentadecylphosphino group, a hexadecylphosphino group, a heptadecylphosphino group, a nonadecylphosphino group, an icosylphosphino group, a cyclopentylphosphino group, a cyclohexylphosphino group, a cycloheptylphosphino group, a dimethylphosphino group, an ethylmethylphosphino group, a diethylphosphino group, a methylpropylphosphino group, a dipropylphosphino group, an ethylhexylphosphino group, a dibutylphosphino group, a heptylmethylphosphino group, a methyloctylphosphino group, a decylmethylphosphino group, a dodecylethylphosphino group, a methylpentadecylphosphino group, an ethyloctadecylphosphino group, a cyclopentylmethylphosphino group, a cyclohexylmethylphosphino group, a cyclohexylethylphosphino group, a cyclohexylpropylphosphino group, a cyclohexylbutylphosphino group and a dicyclohexylphosphino group.

The arylphosphino group includes one, wherein one or two of hydrogen atoms of a phosphino group is each independently replaced by the above aryl group, which is specifically exemplified by a phenylphosphino group, a diphenylphosphino group, a naphthylphosphino group and an anthrylphosphino group.

The alkylphosphinoyl group includes one, wherein one or two of hydrogen atoms of a phosphinoyl group is each independently replaced by the above alkyl group, which is specifically exemplified by a methylphosphinoyl group, an ethylphosphinoyl group, a n-propylphosphinoyl group, an isopropylphosphinoyl group, a n-butylphosphinoyl group, an isobutylphosphinoyl group, a tert-butylphosphinoyl group, a pentylphosphinoyl group, a hexylphosphinoyl group, a heptylphosphinoyl group, an octylphosphinoyl group, a nonylphosphinoyl group, a decylphosphinoyl group, a dodecylphosphinoyl group, a tetradecylphosphinoyl group, a pentadecylphosphinoyl group, a hexadecylphosphinoyl group, a heptadecylphosphinoyl group, a nonadecylphosphinoyl group, a icosylphosphinoyl group, a cyclopentylphosphinoyl group, a cyclohexylphosphinoyl group, a cycloheptylphosphinoyl group, a dimethylphosphinoyl group, an ethylmethylphosphinoyl group, a diethylphosphinoyl group, a methylpropylphosphinoyl group, a dipropylphosphinoyl group, an ethylhexylphosphinoyl group, a dibutylphosphinoyl group, a heptylmethylphosphinoyl group, a methyloctylphosphinoyl group, a decylmethylphosphinoyl group, a dodecylethylphosphinoyl group, a methylpentadecylphosphinoyl group, an ethyloctadecylphosphinoyl group, a cyclopentylmethylphosphinoyl group, a cyclohexylmethylphosphinoyl group, a cyclohexylethylphosphinoyl group, a cyclohexylpropylphosphinoyl group, a cyclohexylbutylphosphinoyl group and a dicyclohexylphosphinoyl group.

The arylphosphinoyl group includes one, wherein one or two of hydrogen atoms of a phosphinoyl group is replaced by the above aryl group, which is specifically exemplified by a phenylphosphinoyl group, a diphenylphosphinoyl group, a naphthylphosphinoyl group and an anthrylphophinoyl group.

The alkylamino group includes one, wherein one or two of hydrogen atoms of an amino group is each independently replaced by the above alkyl group, which is specifically exemplified by a methylamino group, an ethylamino group, a n-propylamino group, an isopropylamino group, a n-butylamino group, an isobutylamino group, a tert-butylamino group, a pentylamino group, a hexylamino group, a heptylamino group, an octylamino group, a nonylamino group, a decylamino group, a dodecylamino group, a tetradecylamino group, a pentadecylamino group, a hexadecylamino group, a heptadecylamino group, a nonadecylamino group, an icosylamino group, a cyclopentylamino group, a cyclohexylamino group, a cycloheptylamino group, a dimethylamino group, an ethylmethylamino group, a diethylamino group, a methylpropylamino group, a dipropylamino group, an ethylhexylamino group, a dibutylamino group, a heptylmethylamino group, a methyloctylamino group, a decylmethylamino group, a dodecylethylamino group, a methylpentadecylamino group, an ethyloctadecylamino group, a cyclopentylmethylamino group, a cyclohexylmethylamino group, a cyclohexylethylamino group, a cyclohexylpropylamino group, a cyclohexylbutylamino group and a dicyclohexylamino group.

The arylamino group includes one, wherein one or two of hydrogen atoms of an amino group is replaced by the above aryl group, which is specifically exemplified by a phenylamino group, a diphenylamino group, a naphthylamino group and an anthrylamino group.

The alkoxycarbonyl group may be straight chained, branched or cyclic, and includes one generally having 2 to 21, preferably 2 to 15, more preferably 2 to 10 and further preferably 2 to 6 carbon atoms, and having further a carbonyl group bonded to an oxygen atom of the above alkoxy group, which is specifically exemplified by a methoxycarbonyl group, an ethoxycarbonyl group, a n-propoxycarbonyl group, a n-butoxycarbonyl group, a tert-butoxycarbonyl group, a pentyloxycarbonyl group, a sec-pentyloxycarbonyl group, a neopentyloxycarbonyl group, a hexyloxycarbonyl group, a cyclohexyloxycarbonyl group, a heptyloxycarbonyl group, a cycloheptyloxycarbonyl group, an octyloxycarbonyl group, a nonyloxycarbonyl group, a decyloxycarbonyl group, a cyclodecyloxycarbonyl group, an undecyloxycarbonyl group, a tetradecyloxycarbonyl group, a heptadecyloxycarbonyl group, a nonadecyloxycarbonyl group, an icosyloxycarbonyl group, a cyclopentyloxycarbonyl group, a cyclohexyloxycarbonyl group, a cyclooctyloxycarbonyl group and a cycloheptadecyloxycarbonyl group.

The aryloxycarbonyl group includes one generally having 7 to 15, preferably 7 to 11 carbon atoms, which is specifically exemplified by a phenyloxycarbonyl group, a naphthyloxycarbonyl group and an anthryloxycarbonyl group.

The alkoxysulfonyl group may be straight chained, branched or cyclic, and includes one generally having 2 to 21, preferably 2 to 15, more preferably 2 to 10 and further preferably 2 to 6 carbon atoms, having further a sulfonyl group bonded to an oxygen atom of the above alkoxy group, which is specifically exemplified by a methoxysulfonyl group, an ethoxysulfonyl group, a n-propoxysulfonyl group, a n-butoxysulfonyl group, a tert-butoxysulfonyl group, a pentyloxysulfonyl group, a sec-pentyloxysulfonyl group, a neopentyloxysulfonyl group, a hexyloxysulfonyl group, a cyclohexyloxysulfonyl group, a heptyloxysulfonyl group, a cycloheptyloxysulfonyl group, an octyloxysulfonyl group, a nonyloxysulfonyl group, a decyloxysulfonyl group, a cyclodecyloxysulfonyl group, an undecyloxysulfonyl group, a tetradecyloxysulfonyl group, a heptadecyloxysulfonyl group, a nonadecyloxysulfonyl group, an icosyloxysulfonyl group, a cyclopentyloxysulfonyl group, a cyclohexyloxysulfonyl group, a cyclooctyloxysulfonyl group and a cycloheptadecyloxysulfonyl group.

The aryloxysulfonyl group includes one generally having 7 to 15, preferably 7 to 11 carbon atoms, which is specifically exemplified by a phenyloxysulfonyl group, a naphthyloxysulfonyl group and an anthryloxysulfonyl group.

The acyl group includes one derived from a carboxylic acid or a sulfonic acid, and the acyl group derived from a carboxylic acid includes one derived from an aliphatic carboxylic acid or an aromatic carboxylic acid. The acyl group derived from a sulfonic acid includes one derived from an aliphatic sulfonic acid or an aromatic sulfonic acid.

The acyl group derived from an aliphatic carboxylic acid may be straight chained, branched or cyclic, and may also have a double bond in the chain, and includes one generally having 2 to 20, preferably 2 to 15, more preferably 2 to 10 and further preferably 2 to 6 carbon atoms, which is specifically exemplified by an acetyl group, a propionyl group, a butyryl group, an isobutyryl group, a valeryl group, an isovaleryl group, a pivaloyl group, a hexanoyl group, a heptanoyl group, an octanoyl group, a decanoyl group, a lauroyl group, a myristoyl group, a palmitoyl group, a stearoyl group, an icosanoyl group, an acryloyl group, a methacryloyl group, a crotonoyl group and an oleoyl group. The acyl group derived from an aromatic carboxylic acid includes one generally having 7 to 15, preferably 7 to 11 carbon atoms, which is specifically exemplified by a benzoyl group, a naphthoyl group and an anthroyl group.

The acyl group derived from an aliphatic sulfonic acid may be straight chained, branched or cyclic, and includes one generally having 1 to 20, preferably 1 to 15, more preferably 1 to 10 and further preferably 1 to 6 carbon atoms, which is specifically exemplified by a methylsulfonyl group, an ethylsulfonyl group, a n-propylsulfonyl group, an isopropylsulfonyl group, a n-butylsulfonyl group, an isobutylsulfonyl group, a tert-butylsulfonyl group, a n-pentylsulfonyl group, a n-hexylsulfonyl group, a heptylsulfonyl group, an octylsulfonyl group, a decylsulfonyl group, a tridecylsulfonyl group, a hexadecylsulfonyl group, an icosylsulfonyl group, a cyclohexylsulfonyl group and a cyclodecylsulfonyl group. The acyl group derived from an aromatic sulfonic acid includes one generally having 6 to 14, preferably 6 to 10 carbon atoms, which is specifically exemplified by a phenylsulfonyl group, a naphthylsulfonyl group and an anthrylsulfonyl group.

The acyloxy group includes an acyloxy group derived from a carboxylic acid having an —O— bonded to the acyl group derived from the above carboxylic acid, and the acyloxy group derived from a sulfonic acid having an —O— bonded to the acyl group derived from the above sulfonic acid. The acyloxy group derived from the carboxylic acid includes an acyloxy group derived from an aliphatic carboxylic acid and an aromatic carboxylic acid. The acyloxy group derived from the sulfonic acid includes an acyloxy group derived from an aliphatic sulfonic acid and an aromatic sulfonic acid.

The acyloxy group derived from the aliphatic carboxylic acid may be straight chained, branched or cyclic and may have further a double bond in the chain, and includes one generally having 2 to 20, preferably 2 to 15, more preferably 2 to 10 and further preferably 2 to 6 carbon atoms, which is specifically exemplified by an acetyloxy group, a propionyloxy group, a butyryloxy group, an isobutyryloxy group, a valeryloxy group, an isovaleryloxy group, a pivaloyloxy group, a hexanoyloxy group, a heptanoyloxy group, an octanoyloxy group, a decanoyloxy group, a lauroyloxy group, a myristoyloxy group, a palmitoyloxy group, a stearoyloxy group, an icosanoyloxy group, an acryloyloxy group, a methacryloyl group, a crotonoyl group, an oleoyloxy group, a cyclohexanoyloxy group and a cyclodecanoyloxy group. The acyloxy group derived from the aromatic carboxylic acid includes one generally having 7 to 15, preferably 7 to 11 carbon atoms, which is specifically exemplified by a benzoyloxy group, a naphthoyloxy group and an anthroyloxy group.

The acyloxy group derived from the aliphatic sulfonic acid may be straight chained, branched or cyclic, and includes one generally having 1 to 20, preferably 1 to 15, more preferably 1 to 10 and further preferably 1 to 6 carbon atoms, which is specifically exemplified by a methylsulfonyloxy group, an ethylsulfonyloxy group, a n-propylsulfonyloxy group, an isopropylsulfonyloxy group, a n-butylsulfonyloxy group, an isobutylsulfonyloxy group, a tert-butylsulfonyloxy group, a n-pentylsulfonyloxy group, a n-hexylsulfonyloxy group, a heptylsulfonyloxy group, an octylsulfonyloxy group, a decylsulfonyloxy group, a tridecylsulfonyloxy group, a hexadecylsulfonyloxy group, an icosylsulfonyloxy group, a cyclopentylsulfonyloxy group and a cyclohexylsulfonyloxy group. The acyloxy group derived from the aromatic sulfonic acid includes one generally having 6 to 14, preferably 6 to 10 carbon atoms, which is specifically exemplified by a phenylsulfonyloxy group, a naphthylsulfonyloxy group and an anthrylsulfonyl group.

The halogen atom includes a chlorine atom, a bromine atom, a fluorine atom and an iodine atom, and among others, a chlorine atom is preferable.

The carboxyl group, the sulfo group, the sulfino group, the sulfeno group, the phosphino group and the phosphinoyl group include also one, wherein a hydrogen atom in these groups is replaced by an alkali metal atom such as sodium, potassium and lithium.

Among the above substituents of the heterocyclic ring, deuteration of a compound having a substituent such as an alkoxycarbonyl group, an aryloxycarbonyl group and a cyano group, which is labile to decomposition under acidic condition, in accordance with the method of the present invention, does not decompose these substituents.

The substituent of a heterocyclic ring which may have a substituent, that is the above alkyl group, alkenyl group, aryl group, aralkyl group, alkoxy group, aryloxy group, alkylthio group, arylthio group, alkylsulfonyl group, arylsulfonyl group, alkylsulfinyl group, arylsulfinyl group, alkylphosphino group, arylphosphino group, alkylphosphinoyl group, arylphosphinoyl group, alkylamino group, arylamino group, alkoxycarbonyl group, aryloxycarbonyl group, alkoxysulfonyl group, aryloxysulfonyl group, acyl group and acyloxy group, may further have a substituent including, for example, an alkyl group, an alkenyl group, an alkynyl group, an aryl group, a hydroxy group, an alkoxy group, an amino group, an alkylamino group, a mercapto group, an alkylthio group, an formyl group, an acyl group, a carboxyl group, an alkoxycarbonyl group, a carbamoyl group and an alkylcarbamoyl group, and these substituents may be present in number of generally 1 to 6, preferably 1 to 4, more preferably 1 to 2 in the substituent of the heterocyclic ring.

The substituent of a heterocyclic ring which may have a substituent, that is an alkyl group, an alkenyl group, an aryl group, an alkoxy group, an alkylamino group, an alkylthio group, an acyl group, a carboxyl group and an alkoxycarbonyl group, includes the same one as the substituent of the above heterocyclic ring which may have a substituent.

The alkynyl group as the substituent of a heterocyclic ring which may have a substituent, may be straight chained, branched or cyclic, and includes one generally having 2 to 20, preferably 2 to 10 and more preferably 2 to 6 carbon atoms, wherein not less than one carbon-carbon triple bond is included in the chain of an alkyl group having not less than two carbon atoms, among the above alkyl groups, which is specifically exemplified by an ethenyl group, a 2-propynyl group, a 2-pentynyl group, a 2-nonyl-3-butynyl group, a cyclohexyl-3-ynyl group, a 4-octynyl group and 1-methyldecyl-5-ynyl group.

The alkylcarbamoyl group as the substituent of a heterocyclic ring which may have a substituent, includes one, wherein one or two of hydrogen atoms of a carbamoyl group is each independently replaced by the above alkyl group, which is specifically exemplified by a methylcarbamoyl group, an ethylcarbamoyl group, a n-propylcarbamoyl group, an isopropylcarbamoyl group, a n-butylcarbamoyl group, an isobutylcarbamoyl group, a tert-butylcarbamoyl group, a pentylcarbamoyl group, a hexylcarbamoyl group, a heptylcarbamoyl group, an octylcarbamoyl group, a nonylcarbamoyl group, a decylcarbamoyl group, a dodecylcarbamoyl group, a tetradecylcarbamoyl group, a pentadecylcarbamoyl group, a hexadecylcarbamoyl group, a heptadecylcarbamoyl group, a nonadecylcarbamoyl group, an icosylcarbamoyl group, a cyclopentylcarbamoyl group, a cyclohexylcarbamoyl group, a dimethylcarbamoyl group, an ethylmethylcarbamoyl group, a diethylcarbamoyl group, a methylpropylcarbamoyl group, a dipropylcarbamoyl group, an ethylhexylcarbamoyl group, a dibutylcarbamoyl group, a heptylmethylcarbamoyl group, a methyloctylcarbamoyl group, decylmethylcarbamoyl group, a dodecylethylcarbamoyl group, a methylpentadecylcarbamoyl group, an ethyloctadecylcarbamoyl group a cyclopentylmethylcarbamoyl group, a cyclohexylmethylcarbamoyl group, a cyclohexylethylcarbamoyl group, a cyclohexylpropylcarbamoyl group, a cyclohexylbutylcarbamoyl group and a dicyclohexylcarbamoyl group.

The compound having a heterocyclic ring in a deuteration method of the present invention includes, a heterocyclic ring itself as described above, or said heterocyclic ring bound with sugar chain, various compounds or polymers, and specific examples of the latter include, for example, nucleosides such as adenosine, deoxyadenosine, guanosine, thymidine, uridine, inosine, deoxyguanosine, deoxythymidine and deoxyuridine; and amino acids such as tryptophan.

In a method for deuteration of the present invention, specific examples of a deuterated solvent used as a heavy hydrogen source to deuterate a heterocyclic ring include, in the case where heavy hydrogen is deuterium, deuterium oxide ($D_2O$), deuterated alcohols such as deuterated methanol, deuterated ethanol, deuterated isopropanol, deuterated butanol, deuterated tert-butanol, deuterated pentanol, deuterated hexanol, deuterated heptanol, deuterated octanol, deuterated nonanol, deuterated decanol, deuterated undecanol and deuterated dodecanol, deuterated carboxylic acids such as deuterated formic acid, deuterated acetic acid, deuterated propionic acid, deuterated butyric acid, deuterated isobutyric acid, deuterated valeric acid, deuterate isovaleric acid and deuterated pivalic acid, deuterated ketones such as deuterated acetone, deuterated methyl ethyl ketone, deuterated methyl isobutyl ketone, deuterated diethyl ketone, deuterated dipropyl ketone, deuterated diisopropyl ketone and deuterated dibutyl ketone, organic solvents such as deuterated dimethylsulfoxide, and among others, deuterium oxide and deuterated alcohols are preferable, and deuterium oxide and deuterated methanol are more preferable, and deuterium oxide is particularly preferable in view of environmental aspect or operability. In the case where heavy hydrogen is tritium, specific examples of a deuterated solvent as a deuteration source include tritium oxide ($T_2O$), etc.

The deuterated solvent may be one wherein at least one hydrogen atom in a molecule is deuterated, and for example, deuterated alcohols wherein at least a hydrogen atom in a hydroxyl group is deuterated, or deuterated carboxylic acids wherein at least a hydrogen atom in a carboxyl group is deuterated, can be used in a method for deuteration of the present invention, and among others, a solvent wherein all hydrogen atoms in a molecule are deuterated is particularly preferable.

As an amount of a deuterated solvent to be used is increasing, deuteration of the present invention tends to proceed further, however, in view of cost, the amount of a deuterated solvent is such level, as lower limit, of generally not less than equimolar, preferably in the order of, not less than 10 molar times, 20 molar times, 30 molar times and 40 molar times, and as upper limit, generally 250 molar times, preferably 150 molar times, of a heavy hydrogen atom contained in the deuterated solvent, relative to hydrogen atoms deuteratable in a compound having a heterocyclic ring as a reactive substrate.

Further, in the case where a compound having a heterocyclic ring as a reactive substrate of a method for deuteration of the present invention is solid which hardly dissolves in a deuterated solvent, a reaction solvent may be used in combination with the deuterated solvent, if necessary.

The specific example of the reaction solvent to be used if necessary, includes organic solvents which are not deuterated with heavy hydrogen gas, containing ethers such as dimethyl ether, diethyl ether, diisopropyl ether, ethylmethyl ether, tert-butylmethyl ether, 1,2-dimethoxyethane, oxirane, 1,4-dioxane, dihydropyrane and tetrahydrofuran; aliphatic hydrocarbons such as hexane, heptane, octane, nonane, decane and cyclohexane; and organic solvents which can be used as heavy hydrogen source of the present invention even if deuterated by heavy hydrogen gas containing water; alcohols such as methanol, ethanol, isopropanol, butanol, tert-butanol, pentanol, hexanol, heptanol, octanol, nonanol, decanol, undecanol and dodecanol; carboxylic acids such as formic acid, acetic acid, propionic acid, butyric acid, isobutyric acid, valeric acid, isovaleric acid and pivalic acid; ketones such as acetone, methylethylketone, methylisobutylketone, diethylketone, dipropylketone, diisopropylketone and dibutylketone; and dimethylsulfoxide.

The activated catalyst selected from a palladium catalyst, a platinum catalyst, a rhodium catalyst, a ruthenium catalyst, a nickel catalyst and a cobalt catalyst in the present invention (hereinafter may be abbreviated as an "activated catalyst") means a so-called palladium catalyst, platinum catalyst, rhodium catalyst, ruthenium catalyst, nickel catalyst or cobalt catalyst (hereinafter may be abbreviated as a "non-activated catalyst" or simply as a "catalyst") which is activated by contact with hydrogen gas or heavy hydrogen gas.

In a method for deuteration of the present invention, deuteration may be carried out using a catalyst activated in advance, or activation of a catalyst and deuteration of reactive substrate may be simultaneously carried out in the co-presence of a non-activated catalyst with hydrogen gas or heavy hydrogen gas in a deuteration reaction system.

When deuteration is carried out using a catalyst activated by hydrogen gas or heavy hydrogen gas in advance, a part of gas phase in a deuteration reactor may be replaced with an inert gas such as nitrogen and argon. When a substrate of the deuteration reaction is hardly reduced with hydrogen gas, and the like, a part of gas phase in a reactor may be replaced with hydrogen gas or heavy hydrogen gas as well as with the above inert gas.

When activation of a catalyst and deuteration of a reactive substrate are simultaneously carried out, the reaction may be conducted after replacing a part of gas phase in a reactor with hydrogen gas or heavy hydrogen gas or directly passing hydrogen gas or heavy hydrogen gas through a reaction solution. Namely, a non-activated catalyst is activated by hydrogen gas or heavy hydrogen gas present in a deuteration reaction system.

In a method for deuteration of the present invention, a reactor is preferably in sealed state or nearly sealed state (hereinafter may be abbreviated as "sealed state") so that the reaction system is, as the result, in pressurized state. Nearly sealed state involves, for example, a case of so-called continuous reaction where a reaction substrate is continuously charged into a reactor and a product is continuously taken out therefrom.

As described above, in a method for deuteration of the present invention, temperature of a reaction system can be easily elevated to perform deuteration efficiently, because the reactor is in sealed state.

Further, when activation of a catalyst and deuteration of a reactive substrate are simultaneously carried out, a complicated process that a catalyst is activated in advance is not required, and also a complicated operation that freeze-pumping is repeated as described in Chem. Commun., 2001,367-368 is not needed.

Furthermore, by using a catalyst activated with hydrogen gas or heavy hydrogen gas in advance for deuteration in sealed state, only deuteration of a substrate proceeds without being reduced at all because hydrogen gas or heavy hydrogen gas is not present in a deuteration reaction system, even the substrate is generally labile to be reduced with hydrogen gas or the like.

The activated catalyst in the present invention includes a palladium catalyst, a platinum catalyst, a rhodium catalyst, a ruthenium catalyst, a nickel catalyst and a cobalt catalyst, as described above, and among others, a palladium catalyst, a platinum catalyst and a rhodium catalyst is preferable, a palladium catalyst and a platinum catalyst is more preferable, and a palladium catalyst is particularly preferable. These catalysts can be used effectively by themselves or in combination accordingly.

The palladium catalyst includes one having generally 0 to 4, preferably 0 to 2 and more preferably 0 valence of a palladium atom.

The platinum catalyst includes one having generally 0 to 4, preferably 0 to 2 and more preferably 0 valence of a platinum atom.

The rhodium catalyst includes one having generally 0 or 1, preferably 0 valence of a rhodium atom.

The ruthenium catalyst includes one having generally 0 to 2, preferably 0 valence of a ruthenium atom.

The nickel catalyst includes one having generally 0 to 2, preferably 0 valence of a nickel atom.

The cobalt catalyst includes one having generally 0 or 1, preferably 1 valence of a cobalt atom.

The above catalyst may be a metal itself of palladium, platinum, rhodium, ruthenium, nickel or cobalt, oxides, halides or acetates of these metals, one which may have a ligand, or may be one consisting of these metals, metal oxides, metal halides, metal acetates or metal complexes supported on various carriers. Hereinafter, a catalyst supported on a carrier may be abbreviated as a "carrier-supported metal catalyst", and a catalyst not supported on a carrier may be abbreviated as a "metal catalyst".

Among catalysts in a method for deuteration of the present invention, a ligand of a metal catalyst which may have a ligand, includes, for example, 1,5-cyclooctadiene (COD), dibenzylideneacetone (DBA), bipyridine (BPY), phenanthroline (PHE), benzonitrile (PhCN), isocyanide (RNC), triethylarsine (As(Et)$_3$), acetylacetonate (acac); organic phosphine ligands such as dimethylphenylphosphine (P(CH$_3$)$_2$Ph), diphenylphosphinoferrocene (DPPF), trimethylphosphine (P(CH$_3$)$_3$), triethylphosphine (PEt3), tri-tert-butylphosphine (PtBu3), tricyclohexylphosphine (PCy$_3$), trimethoxyphosphine (P(OCH$_3$)$_3$), triethoxyphosphine (P(OEt)$_3$), tri-tert-butoxyphosphine (P(OtBu)$_3$), triphenylphosphine (PPh$_3$), 1,2-bis(diphenylphosphino)ethane (DPPE), triphenoxyphosphine (P(OPh)$_3$) and o-tolylphosphine (P(o-tolyl)$_3$).

Specific examples of the palladium based metal catalyst include, for example, Pd; palladium hydroxide catalysts such as Pd(OH)$_2$; palladium oxide catalysts such as PdO; halogenated palladium catalysts such as PdBr2, PdCl$_2$ and PdI$_2$; palladium acetate catalysts such as palladium acetate (Pd(OAc)$_2$) and palladium trifluoroacetate (Pd(OCOCF$_3$)$_2$); palladium metal complex catalysts which are coordinated with a ligand such as Pd(RNC)$_2$Cl$_2$, Pd(acac)$_2$, diacetate-bis-(triphenylphosphine)palladium [Pd(OAc)$_2$(PPh$_3$)$_2$], Pd(PPh$_3$)$_4$, Pd$_2$(dba)$_3$, Pd(NH$_3$)$_2$Cl$_2$, Pd(CH$_3$CN)$_2$Cl$_2$, dichlorobis(benzonitrile)palladium [Pd(PhCN)$_2$Cl$_2$], Pd(dppe)Cl$_2$, Pd(dppf)Cl$_2$, Pd(PCy$_3$)$_2$Cl$_2$, Pd(PPh$_3$)$_2$Cl$_2$, Pd[P(o-tolyl)$_3$]$_2$Cl$_2$, Pd(cod)$_2$Cl$_2$ and Pd(PPh$_3$)(CH$_3$CN)$_2$Cl$_2$.

Specific examples of the platinum based metal catalyst include, for example, Pt; platinum oxide catalysts such as PtO$_2$; halogenated platinum catalysts such as PtCl$_4$, PtCl$_2$ and K$_2$PtCl$_4$; platinum metal complex catalysts which are coordinated with a ligand such as PtCl$_2$(cod), PtCl$_2$(dba), PtCl$_2$(PCy$_3$)$_2$, PtCl$_2$(P(OEt)$_3$)$_2$, PtCl$_2$(P(OtBu)$_3$)$_2$, PtCl$_2$(bpy), PtCl$_2$(phe), Pt(PPh$_3$)$_4$, Pt(cod)$_2$, Pt(dba)$_2$, Pt(bpy)$_2$ and Pt(phe)$_2$.

Specific examples of the rhodium based metal catalyst include, for example, Rh and rhodium metal complex catalysts which are coordinated with a ligand such as RhCl(PPh$_3$)$_3$.

Specific examples of the ruthenium based metal catalyst include, for example, Ru and ruthenium metal complex catalysts which are coordinated with a ligand such as RuCl$_2$(PPh$_3$)$_3$.

Specific examples of the nickel based metal catalyst include, for example, Ni; nickel oxide catalysts such as NiO; halogenated nickel catalysts such as NiCl$_2$; nickel metal complex catalysts which are coordinated with a ligand such as NiCl$_2$(dppe), NiCl$_2$(PPh$_3$)$_2$, Ni(PPh$_3$)$_4$, Ni(P(OPh)$_3$)$_4$ and Ni(cod)$_2$.

Specific examples of the cobalt based metal catalyst include, for example, cobalt metal complex catalysts which are coordinated with a ligand such as Co(C$_3$H$_5$){P(OCH$_3$)$_3$}$_3$.

A carrier, in the case where the above catalyst is supported on a carrier, includes, for example, carbon, alumina, silica gel, zeolite, molecular sieve, ion-exchange resins and polymers, and among others, carbon is preferable.

The ion exchange resin used as a carrier may be one having no adverse effect on deuteration of the present invention, and includes, for example, a cation exchange resin and an anion exchange resin.

The cation exchange resin includes, for example, a weak acidic cation exchange resin and strong acidic cation exchange resin. The anion exchange resin includes, for example, a weak basic anion exchange resin and a strong basic anion exchange resin.

The ion exchange resin generally contains a polymer cross-linked with a bifunctional monomer as a skeleton polymer, to which an acidic group or a basic group is bonded and then is exchanged by various cations and anions (a counter ion), respectively.

Specific examples of the weak acidic cation exchange resin include, for example, one obtained by hydrolysis of a polymer of acrylate ester or a methacrylate ester, cross-linked by divinylbenzene.

Specific examples of the strong acidic cation exchange resin include, for example, one obtained by sulfonation of a copolymer of styrene-divinylbenzene.

Specific examples of the strong basic anion exchange resin include, for example, one wherein an amino group is bonded to an aromatic ring of a copolymer of styrene-divinylbenzene.

Strength of basicity of a basic anion exchange resin increases with an amino group bonded in the order of a primary amino group, a secondary amino group, a tertiary amino group and a quaternary ammonium salt.

The ion exchange resin generally available on the market may be used as well as the above ion exchange resin.

The polymer used as a carrier is not especially limited unless it has serious effects on deuteration of the present invention, however, an example of such a polymer includes, for example, one obtained by polymerization or copolymerization of a monomer shown by the following general formula [1]:

[1]

(wherein $R^1$ is a hydrogen atom, a lower alkyl group, a carboxyl group, a carboxyalkyl group, an alkoxycarbonyl group, a hydroxyalkoxycarbonyl group, a cyano group or a formyl group; $R^2$ is a hydrogen atom, a lower alkyl group, a carboxyl group, an alkoxycarbonyl group, a hydroxyalkoxycarbonyl group, a cyano group or a halogen atom; $R^3$ is a hydrogen atom, a lower alkyl group, a haloalkyl group, a hydroxyl group, an aryl group which may have a substituent, an aliphatic heterocyclic,group an aromatic heterocyclic group, a halogen atom, an alkoxycarbonyl group, a hydroxyalkoxycarbonyl group, a sulfo group, a cyano group, a cyano-containing alkyl group, an acyloxy group, a carboxyl group, a carboxyalkyl group, an aldehyde group, an amino group, an aminoalkyl group, a carbamoyl group, a N-alkylcarbamoyl group or a hydroxyalkyl group, and $R^1$ and $R^2$ may form an alicyclic ring together with the adjacent —C=C— bond).

In the general formula [1], the lower alkyl group shown by $R^1$ to $R^3$ may be straight chained, branched or cyclic, and includes an alkyl group having 1 to 6 carbon atoms, which is specifically exemplified by a methyl group, an ethyl group, a n-propyl group, an isopropyl group, a n-butyl group, an isobutyl group, a tert-butyl group, a sec-butyl group, a n-pentyl group, an isopentyl group, a tert-pentyl group, a 1-methylpentyl group, a n-hexyl group, an isohexyl group, a cyclopropyl group, a cyclopentyl group and a cyclohexyl group.

The carboxyalkyl group shown by $R^1$ and $R^2$ includes one, wherein a part of hydrogen atoms of the above lower alkyl group is replaced by a carboxyl group, which is specifically exemplified by a carboxymethyl group, a carboxyethyl group, a carboxypropyl group, a carboxybutyl group, a carboxypentyl group and a carboxyhexyl group.

The alkoxycarbonyl group shown by $R^1$ to $R^3$ includes preferably one having 2 to 11 carbon atoms, which is specifically exemplified by a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group and a decyloxycarbonyl group.

The hydroxyalkoxycarbonyl group shown by $R^1$ to $R^3$ includes one, wherein a part of hydrogen atoms of the above alkoxycarbonyl group having 2 to 11 carbon atoms is replaced by a hydroxyl group, which is specifically exemplified by a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxynonyloxycarbonyl group and a hydroxydecyloxycarbonyl group.

The halogen atom shown by $R^2$ and $R^3$ includes, for example, fluorine, chlorine, bromine and iodine.

The haloalkyl group shown by $R^3$ includes one having 1 to 6 carbon atoms, wherein the above lower alkyl group shown by $R^1$ to $R^3$ is halogenated (for example, fluorinated, chlorinated, brominated and iodiriated), which is specifically exemplified by a chloromethyl group, a bromomethyl group, a trifluoromethyl group, a 2-chloroethyl group, a 3-chloropropyl group, a 3-bromopropyl group, a 3,3,3-trifluoropropyl group, a 4-chlorobutyl group, a 5-chloropentyl group and a 6-chlorohexyl group.

The aryl group of the aryl group which may have a substituent includes, for example, a phenyl group, a tolyl group, a xylyl group and a naphthyl group, and said substituent includes, for example, an amino group, a hydroxyl group, a lower alkoxy group and a carboxyl group. Specific examples of the substituted aryl group include, for example, an aminophenyl group, a toluidino group, a hydroxyphenyl group, a methoxyphenyl group, a tert-butoxyphenyl group and a carboxyphenyl group.

The aliphatic heterocyclic group includes preferably a 5- or 6-membered one having 1 to 3 hetero atoms such as a nitrogen atom, an oxygen atom and a sulfur atom, which is specifically exemplified by a 2-oxopyrrolidyl group, a piperidyl group, a piperidino group, a piperazinyl group and a morpholino group.

The aromatic heterocyclic group includes preferably a 5- or 6-membered one having 1 to 3 hetero atoms such as a nitrogen atom, an oxygen atom and a sulfur atom, which is specifically exemplified by a pyridyl group, an imidazolyl group, a thiazolyl group, a furyl group and a pyranyl group.

The cyano-containing alkyl group includes one, wherein a part of hydrogen atoms of the above lower alkyl group is replaced by a cyano group, which is specifically exemplified by a cyanomethyl group, a 2-cyanoethyl group, a 2-cyanopropyl group, a 3-cyanopropyl group, a 2-cyanobutyl group, a 4-cyanobutyl group, a 5-cyanopentyl group and a 6-cyanohexyl group.

The acyloxy group includes one derived from a carboxylic acid having 2 to 20 carbon atoms, which is specifically exemplified by an acetyloxy group, a propionyloxy group, a butyryloxy group, a pentanoyloxy group, a nonanoyloxy group, a decanoyloxy group and a benzoyloxy group.

The aminoalkyl group includes one, wherein a part of hydrogen atoms of the above lower alkyl group is replaced by an amino group, which is specifically exemplified by an aminoethyl group, an aminoethyl group, an aminopropyl group, an aminobutyl group, an aminopentyl group and an aminohexyl group.

The N-alkylcarbamoyl group includes one, wherein a part of hydrogen atoms of a carbamoyl group is replaced by an alkyl group, which is specifically exemplified by an N-methylcarbamoyl group, an N-ethylcarbamoyl group, an N-n-propylcarbamoyl group, an N-isopropylcarbamoyl group, an N-n-butylcarbamoyl group and an N-tert-butylcarbamoyl group.

The hydroxyalkyl group includes one, wherein a part of hydrogen atoms of the above lower alkyl group is replaced by a hydroxyl group, which is specifically exemplified by a hydroxymethyl group, a hydroxyethyl group, a hydroxypropyl group, a hydroxybutyl group, a hydroxypentyl group and a hydroxyhexyl group.

The aliphatic ring in the case where $R^1$ and $R^2$ are bonded together with the adjacent —C=C— bond to form an alicyclic ring, includes an unsaturated alicyclic ring having 5 to 10 carbon atoms, and may be monocyclic or polycyclic, which is specifically exemplified by a norbornene ring, a cyclopentene ring, a cyclohexene ring, a cyclooctene ring and a cyclodecene ring.

The specific examples of the monomer shown by the general formula [1] include ethylenically unsaturated aliphatic hydrocarbons having 2 to 20 carbon atoms such as ethylene, propylene, butylene and isobutylene; ethylenically unsaturated aromatic hydrocarbons having 8 to 20 carbon atoms such as styrene, 4-methylstyrene, 4-ethylstyrene and divinylbenzene; alkenyl esters having 3 to 20 carbon atoms such as vinyl formate, vinyl acetate, vinyl propionate and isopropenyl acetate; halogen-containing ethylenically unsaturated compounds having 2 to 20 carbon atoms such as vinyl chloride, vinylidene chloride, vinylidene fluoride and tetrafluoroethylene; ethylenically unsaturated carboxylic acids having 3 to 20 carbon atoms such as acrylic acid, methacrylic acid, itaconic acid, maleic acid, fumaric acid, crotonic acid, vinylacetic acid, allylacetic acid and vinylbenzoic acid (these acids may form an alkali metal salt such as sodium and potassium, or an ammonium salt); ethylenically unsaturated carboxylic acid esters such as methyl methacrylate, ethyl methacrylate, propyl methacrylate, butyl methacrylate, 2-ethylhexyl methacrylate, methyl acrylate, ethyl acrylate, propyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenoate; cyano-containing ethylenically unsaturated compounds having 3 to 20 carbon atoms such as acrylonitrile, methacrylonitrile and allyl cyanide; ethylenically unsaturated amide compounds having 3 to 20 carbon atoms such as acrylamide and methacrylamide; ethylenically unsaturated aldehydes having 3 to 20 carbon atoms such as acrolein and crotonaldehyde; ethylenically unsaturated sulfonic acids having 2 to 20 carbon atoms such as vinylsulfonic acid and 4-vinylbenzene sulfonic acid (these acids may form an alkali metal salts such as sodium and potassium); ethylenically unsaturated aliphatic amines having 2 to 20 carbon atoms such as vinylamine and allylamine; ethylenic unsaturated aromatic amines having 8 to 20 carbon atoms such as vinylaniline; ethylenically unsaturated aliphatic heterocyclic amines having 5 to 20 carbon atoms such as N-vinylpyrrolidone and vinylpiperidine; ethylenically unsaturated alcohols having 3 to 20 carbon atoms such as allyl alcohol and crotyl alcohol; ethylenically unsaturated phenols having 8 to 20 carbon atoms such as 4-vinylphenol, etc.

When the above polymer, and the like is used as a carrier, use of the carrier that is hardly deuterated itself by deuteration of the present invention is preferable, however, a catalyst supported on the carrier deuteratable itself can also be used for deuteration of the present invention.

In a method for deuteration of the present invention, among the above carrier-supported metal catalysts, a palladium carbon, a palladium hydroxide carbon or a platinum carbon are preferably used. Among others, a palladium carbon and a palladium hydroxide carbon are easy in industrial operability and have superior catalytic activity, and in particular, use of a palladium carbon mostly provides further efficient deuteration reaction.

In the carrier-supported catalyst, content of the catalyst metal which is palladium, platinum, rhodium, ruthenium, nickel and cobalt, is generally 1 to 99% by weight, preferably 1 to 50% by weight, more preferably 1 to 30% by weight, further more preferably 1 to 20% by weight, and particularly preferably 5 to 10% by weight based on whole catalyst.

In a method for deuteration of the present invention, amount of the activated catalyst or non-activated catalyst to be used is generally so-called catalyst quantity, preferably in the order of, 0.01 to 200% by weight, 0.01 to 100% by weight, 0.01 to 50% by weight, 0.01 to 20% by weight, 0.1 to 20% by weight, 1 to 20% by weight and 10 to 20% by weight, relative to a compound having a heterocyclic ring to be used as a reactive substrate, irrespective of whether the catalyst is supported by a carrier or not, and upper limit content of the catalyst metal in said whole catalyst is preferably in the order of, 20% by weight, 10% by weight, 5% by weight and 2% by weight, while lower limit thereof is preferably in the order of, 0.0005% by weight, 0.005% by weight, 0.05% by weight and 0.5% by weight.

When a compound having a heterocyclic ring is deuterated, 2 or more kinds of various catalysts as described above can be used in an appropriate combination.

In the case where 2 or more kinds of catalysts are used in combination, amount of the catalysts to be used may be set so that total amount of the catalysts becomes the amount of the catalyst to be used as described above.

In the case when a non-activated catalyst is used in a reaction of the present invention, amount of hydrogen to be used when hydrogen gas is present in a reaction system to activate the non-activated catalyst may be a little more than necessary amount to activate the catalyst to efficiently carry out activation of the catalyst, though there is possibility that excessive amount of hydrogen shows adverse effect on a deuteration reaction of the present invention such as hydrogenation of a deuterated solvent as heavy hydrogen source. Such amount of hydrogen gas is generally 1 to 20,000 equivalents and preferably 10 to 700 equivalents, relative to the catalyst.

Amount of heavy hydrogen to be used when heavy hydrogen is present in a reaction system to activate the non-activated catalyst may be necessary amount to activate the catalyst, generally 1 to 20,000 equivalents and preferably 10 to 700 equivalents, relative to the catalyst, however, even if amount of said heavy hydrogen is excessively large, deuteration of the present invention can be performed without any problem, because said heavy hydrogen is in contact with a deuterated solvent in a reaction system and has effect to further deuterate said solvent.

In a method for deuteration of the present invention, reaction temperature may be determined so that a reaction system is in refluxing state at temperature higher than boiling point (at atmospheric pressure) of the solvent, and lower limit of such reaction temperature is preferably in the order of, +3° C., +5° C., +10° C. and +20° C. exceeding boiling point of the solvent, and upper limit thereof is preferably in the order of, +100° C., +80° C., +70° C. and +60° C. exceeding boiling point of the solvent.

Setting of the above reaction temperature in a reactor in sealed state may be performed by heating and/or pressurizing, thereby to make inside of the reaction system in pressurized state.

Pressurization of a reaction system may be performed using hydrogen gas to activate a catalyst, or may be performed using further inert gas such as nitrogen gas and argon gas.

Reaction time in a method for deuteration of the present invention is generally 30 minutes to 100 hours, preferably 1 to 50 hours, more preferably 1 to 30 hours and further more preferably 3 to 30 hours.

A method for deuteration of the present invention will be specifically explained by taking, as an example, the case of using heavy water as heavy hydrogen source and using a palladium catalyst as a non-activated catalyst.

For example, a compound having a heterocyclic ring (substrate) and a palladium catalyst are added to a deuterated solvent, followed by sealing the reaction system, replacing atmosphere in the reaction system with hydrogen gas and reacting with stirring in an oil bath at about 103 to 200° C. for about 30 minutes to 100 hours. After completion of the reaction, when the reaction product is soluble in a deuterated solvent, the catalyst is filtered off from the reaction solution, and the filtrate is subjected to, as it is, structural analysis by $^1$H-NMR, $^2$H-NMR and mass spectrum measurements. When the reaction product is hardly soluble in the deuterated solvent, the reaction product is isolated from the reaction solution to be subjected to structural analysis by $^1$H-NMR, $^2$H-NMR and mass spectrum measurements.

When the product is hardly soluble in a deuterated solvent, the isolation of the product from the reaction solution may be carried out according to known purification methods such as extraction of the product from the reaction solution using an organic solvent in which the product is soluble and then filtering off the catalyst.

Even when a compound having a heterocyclic ring contains a halogen atom as a substituent, only the heterocyclic ring can be deuterated without the above halogen atom being substituted by a hydrogen atom or a deuterium atom, or even when the compound having a heterocyclic ring contains a substituent such as a nitro group and a cyano group, only the heterocyclic ring can be deuterated without the above substituent being reduced, by performing a method for deuteration of the present invention using a catalyst activated in advance as an activated catalyst and a deuterated solvent as heavy hydrogen source.

As described above, in accordance with a method for deuteration of the present invention which comprises subjecting a compound having a heterocyclic ring to sealed refluxing state in a deuterated solvent in the presence of an activated catalyst, a hydrogen atom belonging to the heterocyclic ring of a compound having a heterocyclic ring can be deuterated very efficiently because deuteration reaction temperature can be maintained at higher than boiling point of the solvent.

Further, in accordance with a method for deuteration of the present invention, not only a hydrogen atom belonging to a heterocyclic ring, but also a hydrogen atom belonging to a carbon atom present in a substituent of a heterocyclic ring (for example, one derived from an alkyl group, an alkenyl group, an aralkyl group, an alkoxy group, an alkylthio group, an alkylsulfonyl group, an alkylsulfinyl group, an alkylphosphino group, an alkylphosphinoyl group, an alkylamino group, an alkoxycarbonyl group, an alkoxysulfonyl group and an acyl group) or a hydrogen atom bound to a carbon atom present in a sugar chain, various compounds or polymers, bound to a heterocyclic ring can also be deuterated.

In the following, the present invention is explained in further detail referring to Examples, but the present invention is not limited thereto by any means.

Further, in the following Examples, isolation yield means yield of a compound isolated after completion of the reaction irrespective of whether deuterated or not, and deuteration ratio means ratio of amount of deuterated atoms to amount of deuteratable hydrogen atoms in a compound isolated after completion of the reaction. In the following Examples, deuteration ratio of a hydrogen atom in each position of an isolated compound is shown.

EXAMPLE

Example 1

In 17 mL of deuterium oxide ($D_2O$) were suspended 500 mg of imidazol and 50 mg of palladium carbon (Pd 10%), followed by replacing atmosphere of a sealed reaction system with hydrogen gas and conducting a reaction in an oil bath at 160° C. for about 24 hours. After completion of the reaction, the reaction solution was extracted with ether, followed by filtering out the catalyst and concentration of the filtrate under reduced pressure to obtain 500 mg of deuterated compound (isolation yield 95%). Structural analysis of thus obtained compound by $^1$H-NMR, $^2$H-NMR and mass spectrum measurements gave the following deuteration ratios for each hydrogen atom of the compound obtained. Deuteration ratio to total hydrogen atoms in the position (1) shown by the following formula was 99%, and deuteration ratio to total hydrogen atoms in the position (2) was also 99%.

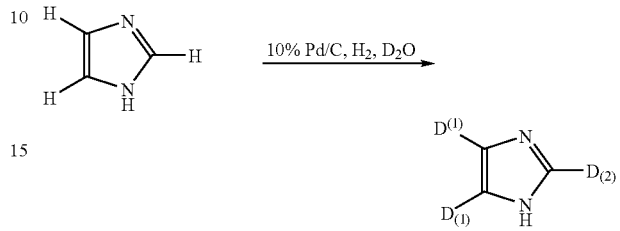

Examples 2 to 5

Similar deuteration reactions as in Example 1 were conducted except for using substrates shown in the following Table 1. Isolation yields and deuteration ratios of each deuterated compound are shown in Table 1. Hereinafter, deuteration ratios in each Example were calculated in the same manner as in Example 1.

TABLE 1

| | Reactive substrate | Product | Isolation yield (%) | Deuteration ratio (%) |
|---|---|---|---|---|
| Example 2 | imidazole with 2-CH₃ | imidazole with 2-CD₃, D at (1), (1), (2) | 99 | (1) 99 (2) 99 |
| Example 3 | imidazole with 2-CH(CH₃) | deuterated product | 86 | (1) 99 (2) 91 (3) 79 |
| Example 4 | 4-methylimidazole | deuterated product | 92 | (1) 98 (2) 94 |
| Example 5 | 1-methylimidazole | deuterated product | 72 | (1) 99 (2) 99 (3) 99 |

Examples 6 to 7

Similar deuteration reactions as in Example 1 were conducted except for using adenine as a substrate and conducting the reactions under reaction conditions shown in the following Table 2. Isolation yields and deuteration ratios of the obtained compounds are shown together in Table 2.

TABLE 2

|  | Reaction temperature | Reaction time | Isolation yield (%) | Deuteration ratio (%) |
|---|---|---|---|---|
| Example 6 | 110° C. | 24 hours | 94 | 48 |
| Example 7 | 140° C. | 48 hours | 36 | 95 |

Deuteration ratio in Table 2 is ratio of amount of total deuterated atoms to amount of total deuteratable hydrogen atoms in the positions of (1) and (2) in the above chemical formula.

Examples 8 to 9

Similar deuteration reactions as in Example 1 were conducted except for using adenosine as a substrate and carrying out the reactions under reaction conditions shown in the following Table 3. Isolation yields and deuteration ratios of the obtained compounds are shown together in Table 3.

TABLE 3

|  | Reaction temperature | Reaction time | Isolation yield (%) | Deuteration ratio (%) |
|---|---|---|---|---|
| Example 8 | 110° C. | 48 hours | 99 | (1) 94, (2) 92 |
| Example 9 | 140° C. | 48 hours | 74 | (1) 91, (2) 91 |

Examples 10 to 12

Similar deuteration reactions as in Example 1 were conducted except for using guanosine as a substrate and carrying out the reactions under reaction conditions shown in the following Table 4. Isolation yields and deuteration ratios of the obtained compounds are shown together in Table 4.

TABLE 4

|  | Reaction temperature | Reaction time | Isolation yield (%) | Deuteration ratio (%) |
|---|---|---|---|---|
| Example 10 | 110° C. | 48 hours | 94 | (1) 94 |
| Example 11 | 140° C. | 48 hours | 99 | (1) 93 |
| Example 12 | 160° C. | 24 hours | 98 | (1) 96 |

Examples 13 to 14

Similar deuteration reactions as in Example 1 were conducted except for using thymine as a substrate and carrying out the reactions under reaction conditions shown in the following Table 5. Isolation yields and deuteration ratios of the obtained compounds are shown together in Table 5.

TABLE 5

|  | Reaction temperature | Reaction time | Isolation yield (%) | Deuteration ratio (%) |
|---|---|---|---|---|
| Example 13 | 110° C. | 24 hours | 96 | (1) 99, (2) 64 |
| Example 14 | 140° C. | 48 hours | 65 | (1) 96, (2) 94 |

Example 15

Similar deuteration reaction as in Example 1 was conducted except for using cytosine as a substrate and carrying out the reaction at 160° C. for 48 hours. Isolation yield of the obtained compound was 98% and deuteration ratios thereof were (1) 96% and (2) 96%.

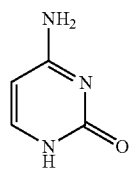

Example 16

Similar deuteration reaction as in Example 1 was conducted except for using uracil as a substrate and carrying out the reaction at 160° C. for 48 hours. Isolation yield of the obtained compound was 94% and deuteration ratios thereof were (1) 98% and (2) 93%.

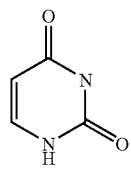

Example 17

Similar deuteration reaction as in Example 1 was conducted except for using uridine as a substrate and carrying out the reaction at 160° C. for 24 hours in a sealed state. Isolation yield of the obtained compound was 85% and deuteration ratios thereof were (1) 48% and (2) 95%.

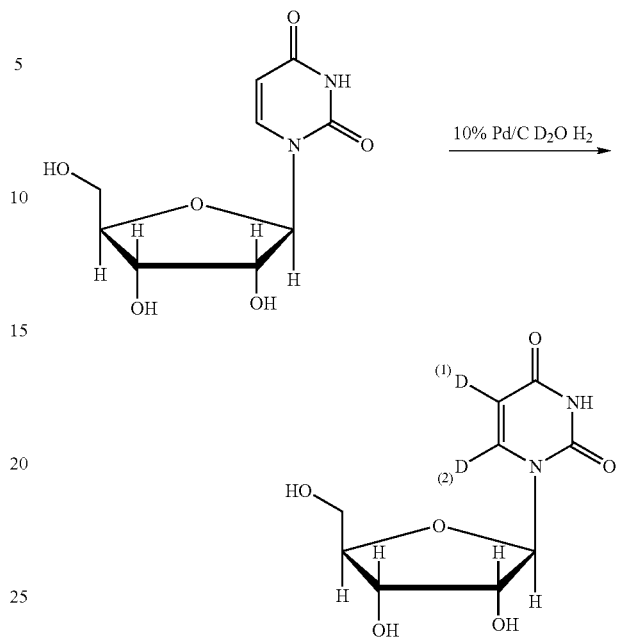

Examples 18 to 19

Similar deuteration reactions as in Example 1 were conducted except for using inosine as a substrate and carrying out the reactions under reaction conditions shown in the following Table 6. Isolation yields and deuteration ratios of the obtained compounds are shown together in Table 6.

TABLE 6

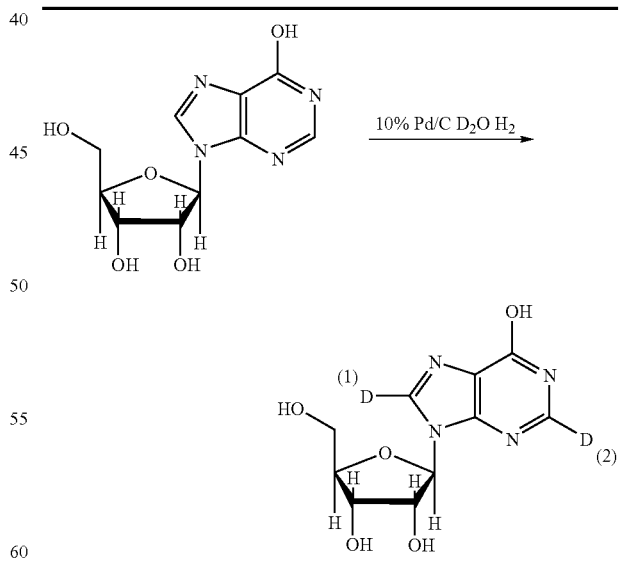

| | Reaction temperature | Reaction time | Isolation yield (%) | Deuteration ratio (%) |
|---|---|---|---|---|
| Example 18 | 110° C. | 48 hours | 98 | (1) 79, (2) 84 |
| Example 19 | 140° C. | 48 hours | 90 | (1) 85, (2) 97 |

Example 20

Similar deuteration reaction as in Example 1 was conducted except for using hypoxanthine as a substrate and carrying out the reaction at 110° C. for 48 hours. Isolation yield of the obtained compound was 62% and deuteration ratio thereof to total deuteratable hydrogen atoms in the positions (1) and (2) was 95%.

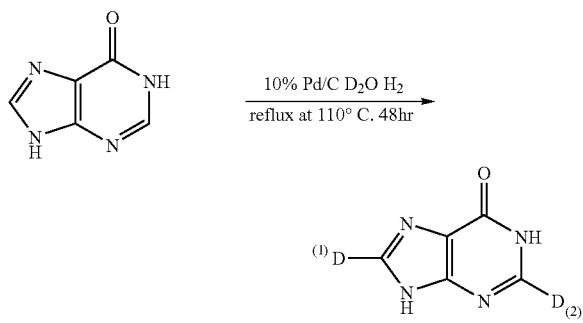

Examples 21 to 22

Similar deuteration reactions as in Example 1 were conducted except for using 3-methylindole as a substrate and carrying out the reactions under reaction conditions shown in the following Table 7. Isolation yields and deuteration ratios of the obtained compounds are shown together in Table 7.

TABLE 7

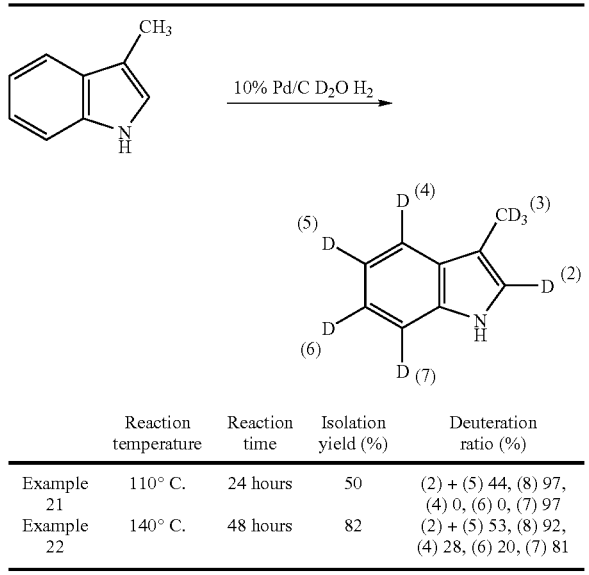

| | Reaction temperature | Reaction time | Isolation yield (%) | Deuteration ratio (%) |
|---|---|---|---|---|
| Example 21 | 110° C. | 24 hours | 50 | (2) + (5) 44, (8) 97, (4) 0, (6) 0, (7) 97 |
| Example 22 | 140° C. | 48 hours | 82 | (2) + (5) 53, (8) 92, (4) 28, (6) 20, (7) 81 |

Deuteration ratio of (2)+(5) in Table 7 means a deuteration ratio to total deuteratable hydrogen atoms in the positions of (2) and (5).

Example 23

Similar deuteration reaction as in Example 1 was conducted except for using 5-methylindole as a substrate and carrying out the reaction at 140° C. for 48 hours. Isolation yield of the obtained compound was 65% and deuteration ratios thereof were (2) 100%, (3) 90%, (4) 27%, (5) 95%, (6) 99% and (7) 38%.

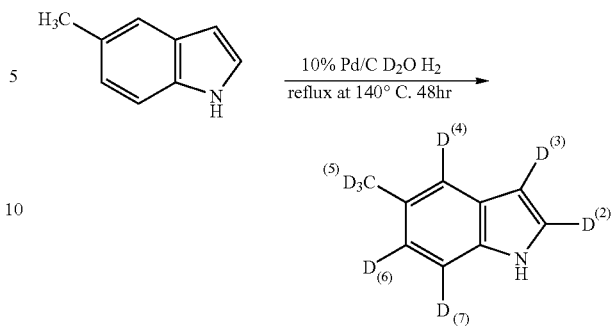

Example 24

Similar deuteration reaction as in Example 1 was conducted except for using 7-methylindole as a substrate and carrying out the reaction at 140° C. for 48 hours. Isolation yield of the obtained compound was 79% and deuteration ratios thereof were (2) 96%, (3) 95%, (4) 95%, (5)+(6) 59% and (7) 96%.

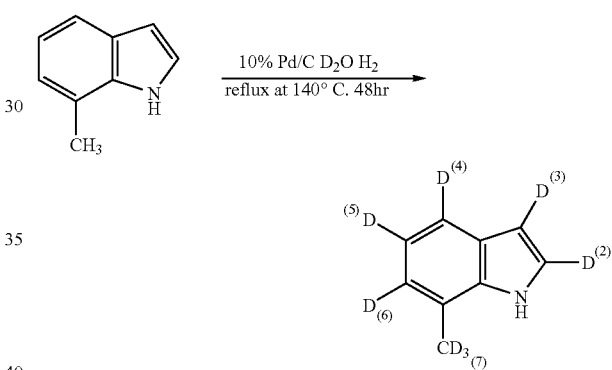

Example 25

Similar deuteration reaction as in Example 1 was conducted except for using 3,5-dimethylpyrazole as a substrate and carrying out the reaction at 140° C. for 48 hours. Isolation yield of the obtained compound was 55% and deuteration ratios thereof were (3)+(5) 96% and (4) 95%.

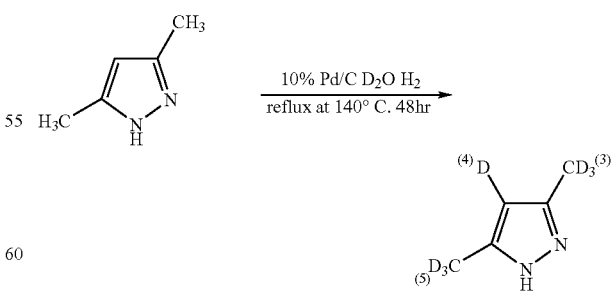

Example 26

Similar deuteration reaction as in Example 1 was conducted except for using 5-methylbenzimidazole as a substrate and carrying out the reaction at 140° C. for 48 hours. Isolation yield of the obtained compound was 99% and deuteration ratios thereof were (2) 98%, (4) 98%, (5) 95%, (6) 19% and (7) 98%.

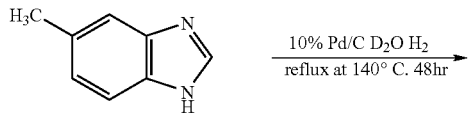

Example 27

Similar deuteration reaction as in Example 1 was conducted except for using 7-azaindole as a substrate and carrying out the reaction at 140° C. for 48 hours. Isolation yield of the obtained compound was 92% and deuteration ratios thereof were (2) 95%, (3) 94%, (4) 94%, (5) 69% and (6) 96%.

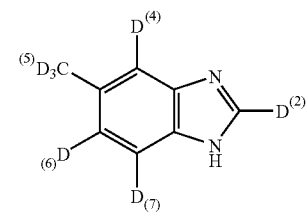

Example 28

Similar deuteration reaction as in Example 1 was conducted except for using L-tryptophan as a substrate and carrying out the reaction at 160° C. for 48 hours. Isolation yield of the obtained compound was 93% and deuteration ratios thereof were (1) 45%, (2) 47%, (3)+(4) 22% and (5) 0%.

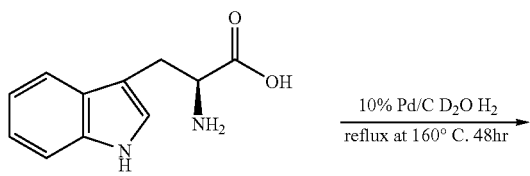

-continued

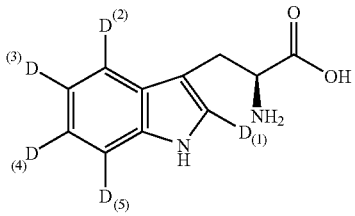

Example 29

Similar deuteration reaction as in Example 1 was conducted except for using 2,3-rutidine as a substrate and carrying out the reaction at 160° C. for 6 hours. Isolation yield of the obtained compound was 74% and deuteration ratio to total deuteratable hydrogen atoms in the positions (1) to (5) was 98%.

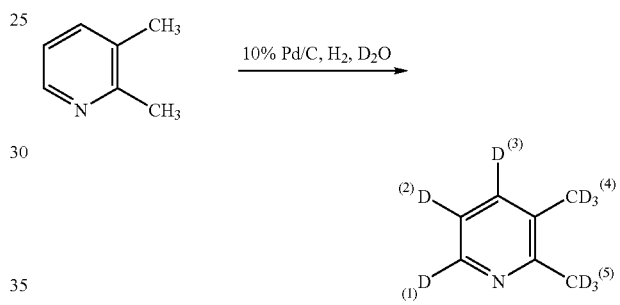

Example 30

Similar deuteration reaction as in Example 1 was conducted except for using 2-methylimidazole as a substrate and carrying out the reaction at 120° C. for 24 hours. Isolation yield of the obtained compound was 99% and deuteration ratios thereof were (1) 99% and (2) 20%.

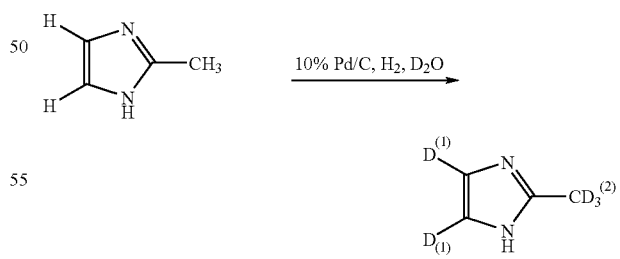

Example 31

Similar deuteration reaction as in Example 30 was conducted except for using heavy methanol instead of heavy water. Isolation yield of the obtained compound was 88% and deuteration ratios thereof were (1) 86% and (2) 9%.

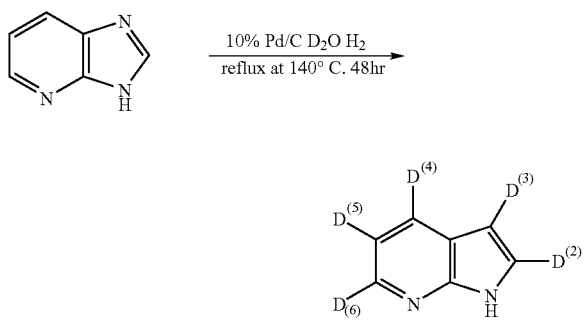

As obvious from the results of Examples 30 and 31, a deuterated organic solvent can also be used as well as heavy water in a method for deuteration of the present invention.

Example 32

Similar deuteration reaction as in Example 1 was conducted except for using 2-methylimidazole as a substrate and a platinum carbon (Pt 5%) instead of a palladium carbon. Isolation yield of the obtained compound was 95% and deuteration ratios thereof were (1) 93% and (2) 67%.

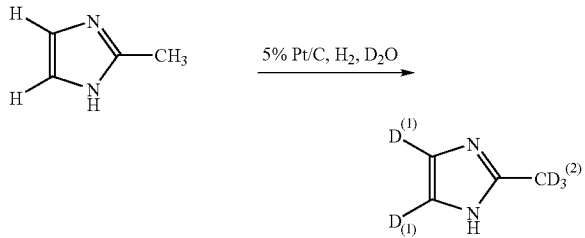

INDUSTRIAL APPLICABILITY

In accordance with a method for deuteration of the present invention, which comprises subjecting a compound having a heterocyclic ring to sealed refluxing state in a deuterated solvent in the presence of an activated catalyst, a hydrogen atom belonging to the heterocyclic ring of the compound having a heterocyclic ring can be very easily deuterated because temperature of deuteration reaction can be maintained at not lower than boiling point of the solvent.

Further, a method for deuteration of the present invention can be applied widely to deuteration of various compounds having a heterocyclic ring which are liable to decomposition under supercritical conditions or acidic conditions, leading to industrial and efficient deuteration of a compound having a heterocyclic ring.

What is claimed is:

1. A method for deuteration of a heterocyclic ring, which comprises subjecting a compound having a heterocyclic ring to a sealed refluxing state in a deuterated solvent in the presence of an activated palladium catalyst.

2. The method for deuteration according to claim 1, wherein the activated palladium catalyst is an activated palladium carbon.

3. The method for deuteration according to claim 1, wherein the activated palladium catalyst is one activated with hydrogen gas or heavy hydrogen gas present in a deuteration reaction system.

4. The method for deuteration according to claim 1, wherein the deuterated solvent is heavy water ($D_2O$).

5. The method for deuteration according to claim 1, wherein the heterocyclic ring of the compound having a heterocyclic ring is a 3 to 20 membered ring.

* * * * *